United States Patent
Stauffer

(10) Patent No.: US 7,285,689 B2
(45) Date of Patent: Oct. 23, 2007

(54) PHENOL PROCESS

(76) Inventor: John E. Stauffer, 6 Pecksland Rd., Greenwich, CT (US) 06830

( * ) Notice: Subject to any disclaimer, the term of this patent is extended or adjusted under 35 U.S.C. 154(b) by 55 days.

(21) Appl. No.: 11/361,178

(22) Filed: Feb. 24, 2006

(65) Prior Publication Data

US 2007/0203370 A1  Aug. 30, 2007

(51) Int. Cl.
*C07C 37/00* (2006.01)
(52) U.S. Cl. ..................................................... 568/796
(58) Field of Classification Search ...................... None
See application file for complete search history.

(56) References Cited

U.S. PATENT DOCUMENTS

| | | | |
|---|---|---|---|
| 1,963,761 A | 6/1934 | Prahl | 260/161 |
| 2,035,917 A | 3/1936 | Prahl et al. | 260/154 |
| 2,311,777 A * | 2/1943 | Redman | 568/797 |

\* cited by examiner

*Primary Examiner*—Johann Richter
*Assistant Examiner*—Kellette Gale
(74) *Attorney, Agent, or Firm*—Young & Basile, P.C.

(57) ABSTRACT

A process is provided for the production of phenol from chlorobenzene. The process comprises a chemical reaction in which chlorobenzene is reacted with an alcohol in the vapor phase to form phenol and the corresponding alkyl chloride. A catalyst is used to promote the reaction. Among the alcohols used are methyl alcohol and ethyl alcohol.

8 Claims, 1 Drawing Sheet

PHENOL PROCESS

FIELD OF THE INVENTION

The present invention relates to a process for producing phenol from chlorobenzene. This process employs a unique chemical reaction whereby chlorobenzene is reacted with an alcohol to provide phenol and an alkyl chloride. The group of alcohols used includes methyl alcohol and ethyl alcohol.

BACKGROUND OF THE INVENTION

Since the middle of the nineteenth century phenol has been an important item of commerce. Initially it was recovered from coal tar, which was its only source for many years. As the demand for phenol increased, synthetic processes were introduced to make this chemical.

One of the earliest phenol processed was the so-called Raschig Process. First, benzene was oxychlorinated with hydrogen chloride and oxygen to produce chlorobenzene. Second, the chlorobenzene from the first step was hydrolyzed with water to form phenol and hydrogen chloride. By recycling the hydrogen chloride so produced to the first step, a self-contained process resulted.

The details of the Raschig Process are outlined in U.S. Pat. No. 1,963,761 U.S. Pat. No. 2,035,917 and U.S. Pat. No. 2,311,777. Although no longer in use, the Raschig Process proved to be a commercial success. The chief difficulties with the process involve the hydrolysis step. The hydrochloric acid produced is extremely corrosive and requires expensive equipment to handle. The hydrolysis reaction is reversible, thus limiting the conversion of chlorobenzene to phenol. Lastly, by-product formation adds to the cost of manufacture.

With the drawbacks of the Raschig Process in mind, the present invention was conceived as an improved process for the production of phenol. The objects of the present invention includes a process that meets the environmental and economic needs of manufacturers. These objects as well as other features and advantages will be apparent from the following description and the figure, which is included.

SUMMARY OF THE DISCLOSURE

The specification covers a process for the synthesis of phenol from chlorobenzene. A novel chemical reaction is employed in the process. Chlorobenzene is reacted with an alcohol in the vapor phase to provide phenol and the corresponding alkyl chloride. Because of their availability, the preferred alcohols are methyl alcohol and ethyl alcohol.

The reaction requires a heterogeneous catalyst for optimum results. This catalyst can be selected from a large group of compounds. The preferred catalysts include salts of magnesium, aluminum, calcium, copper, zinc and bismuth. The negative radical includes the elements silicon, phosphorus, sulfur, and chlorine. Thus, calcium phosphate meets the requirements for a catalyst. In addition to the above compounds, the catalyst may comprise alumina gel, silica, or a silica-alumina catalyst.

A wide temperature range may be used for the reaction. Preferably the reaction temperature should be between about 275° and about 500° C., but these limits should not be binding. Above 500° C. the reaction will take place, however, with the formation of byproducts. Below 275° C. the rate of reaction becomes excessively slow.

The reaction is exothermic so that means for removing the heat of reaction must be provided. This objective can be met by using any one of several reactor designs that contribute to efficient heat transfer. In this manner, the reaction temperature can be precisely controlled.

DETAILED DESCRIPTION OF THE PROCESS

Figure 1:
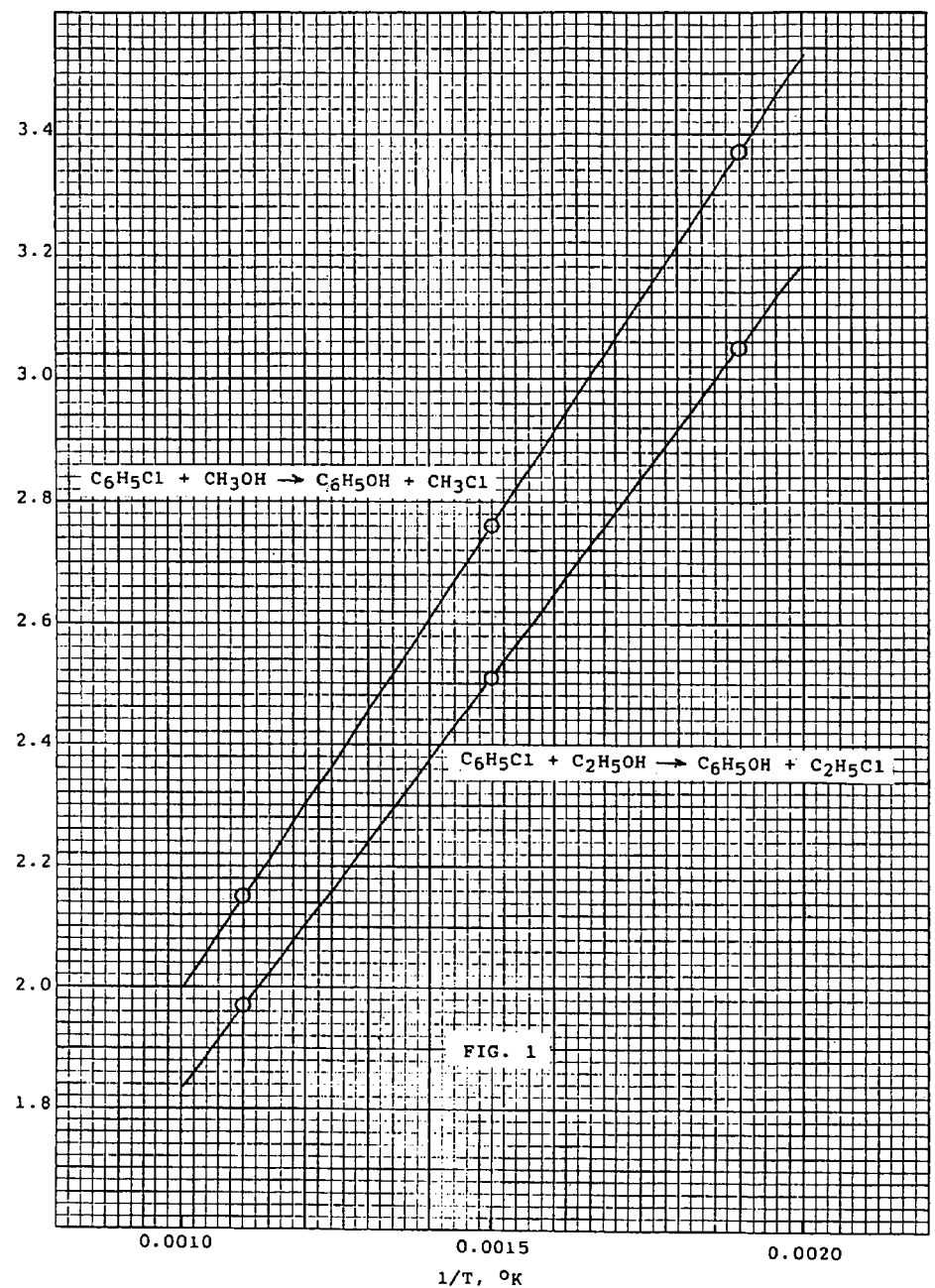
FIG. 1 is a graph showing the equilibrium conversions for the reaction of the present invention at various temperatures when methyl alcohol is reacted with chlorobenzene, and when ethyl alcohol is used.

The process of the present invention can be generalized by the following equation:

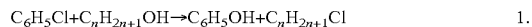

where $C_6H_5Cl$ is chlorobenzene $C_nH_{2n+1}OH$ is the alcohol used $C_6H_5OH$ is phenol, and $C_nH_{2n+1}Cl$ is alkyl chloride.

In the special case where methyl alcohol is used, the reaction can be written as follows:

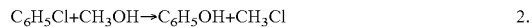

where $CH_3OH$ is methyl alcohol and $CH_3Cl$ is methyl chloride.

Likewise, in the case where ethyl alcohol is the reactant, the following reaction takes place:

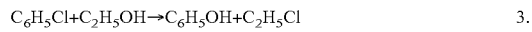

where $C_6H_5OH$ is the ethyl alcohol and $C_2H_5Cl$ is the ethyl chloride.

The conversions of chlorobenzene to phenol under equilibrium conditions can be determined by thermodynamic calculations. Unfortunately data for the standard enthalpy and the standard Gibbs Energy of Formation for chlorobenzene in the gas phase is missing from the literature. These thermodynamic data, however, are available for both benzene and 1,4-dichlorobenzene. By assuming that the change in enthalpy for the chlorination of benzene to chlorobenzene is the same as the change in enthalpy for the chlorination of chlorobenzene to 1,4-dichlorobenzene, a value for the standard enthalpy of chlorobenzene can be determined. The result of this calculation was 52.55 kJ per mol. In a similar manner, the standard Gibbs Energy of Formation for chlorobenzene was determined to be 103.45 kJ per mol.

Using the calculated data for chlorobenzene as well as the reported data for alcohols and the products of the reaction, it was possible to calculate equilibrium constants at different reaction temperatures. In the reaction of chlorobenzene with methyl alcohol, the logarithm of the equilibrium constant $K_p$ equals 3.37 at 250° C., 2.76 at 400° C., and 2.15 at 600° C. Similarly, log $K_p$ for the reaction with ethyl alcohol is 3.05 at 250° C., 2.51 at 400°, and 1.97 at 600° C.

These data are plotted in FIG. 1. In all cases, the results are highly favorable for the formation of phenol. While data were not calculated for propyl alcohol, similar results would be expected.

The reaction of the present invention requires a catalyst to proceed. In order to determine an effective catalyst, a mechanism or model for the reaction was postulated. The reaction can be considered the result of two separate reactions shown as follows for the use of methyl alcohol:

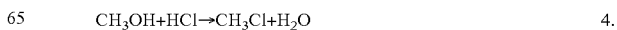

where HCl is a hydrogen chloride and H₂O is water. When equations 4 and 5 are combined the result is the same as equation 2.

The reaction conditions are known for both reactions represented by equations 4 and 5. In the case given by equation 4, methyl alcohol will react with hydrogen chloride in the vapor phase of a temperature in the range of 280° C. to 350° C. Effective catalysts for this reaction include alumina gel as well as the chlorides of copper, zinc, and bismuth.

The hydrolysis of chlorobenzene shown in equation 5 is promoted by salts of magnesium, aluminum, calcium, and copper, and zinc. The negative radical includes the elements silicon, phosphorous, sulfur, and chlorine. In addition, catalytically active silicic acid is effective. The reaction takes place over a wide temperature range with results being reported in the range of 275° C. to 500° C.

As can be seen from the reported data, there is considerable overlap in the conditions favorable to the reactions represented by equations 4 and 5. This commonality provides the basis for the specifications of the present invention.

The chlorobenzene required by the process of the present invention can be supplied from several sources. In one instance, benzene is chlorinated with chlorine to produce chlorobenzene. An alternative approach is to oxychlorinate benzene with hydrogen chloride and oxygen to give chlorobenzene.

By product alkyl chloride finds use in commerce. For example, large quantities of methyl chloride are used in the manufacture of silicones. Attractive economics for the process are thus assured.

The invention in which exclusive property or privilege is claimed is defined as follows:

1. A process for the manufacture of phenol comprising the reaction of chlorobenzene with an alcohol in the vapor phase to produce phenol and the corresponding alkyl chloride.

2. A process according to claim 1 in which the alcohol is methyl alcohol.

3. A process according to claim 1 in which the alcohol is ethyl alcohol.

4. A process according to claim 1 in which a catalyst is used in the reaction.

5. A process according to claim 4 in which the catalyst comprises a silica-alumina catalyst.

6. A process according to claim 4 in which the catalyst comprises copper chloride.

7. A process according to claim 4 in which the catalyst comprises zinc chloride.

8. A process according to claim 1 in which the reaction is carried out at a temperature in the range of about 275° C. to about 500° C.

* * * * *